United States Patent [19]

Leak et al.

[11] Patent Number: 5,763,041
[45] Date of Patent: Jun. 9, 1998

[54] LAMINATE MATERIAL

[75] Inventors: A. Todd Leak, Neenah; Mark Michael Mleziva, Whitelaw; Duane Girard Uitenbroek, Little Chute, all of Wis.; Monica Signoret Diaz, Woodstock; Lance James Garrett, Jr., Marietta, both of Ga.

[73] Assignee: Kimberly-Clark Worldwide, Inc., Neenah, Wis.

[21] Appl. No.: 576,181

[22] Filed: Dec. 21, 1995

[51] Int. Cl.$^6$ ............................................. B32B 3/06
[52] U.S. Cl. ..................... 428/100; 24/447; 428/186; 428/198; 604/378; 604/393
[58] Field of Search ........................ 428/99, 100, 198, 428/284, 286, 296, 297, 298, 152, 186, 131, 246; 24/447; 604/378, 393

[56] References Cited

U.S. PATENT DOCUMENTS

| | | | |
|---|---|---|---|
| 3,276,944 | 10/1966 | Levy | 161/150 |
| 3,338,992 | 8/1967 | Kinney | 264/24 |
| 3,341,394 | 9/1967 | Kinney | 161/72 |
| 3,464,876 | 9/1969 | Barb | 156/155 |
| 3,502,538 | 3/1970 | Petersen | 161/150 |
| 3,502,763 | 3/1970 | Hartmann | 264/210 |
| 3,507,943 | 4/1970 | Such et al. | 264/103 |
| 3,542,615 | 11/1970 | Dobo et al. | 156/181 |
| 3,668,054 | 6/1972 | Stumpf | 161/128 |
| 3,689,353 | 9/1972 | Spiegelberg et al. | 161/63 |
| 3,692,618 | 9/1972 | Dorschner et al. | 161/72 |
| 3,694,867 | 10/1972 | Stumpf | 24/204 |
| 3,705,063 | 12/1972 | Stumpf | 156/72 |

(List continued on next page.)

FOREIGN PATENT DOCUMENTS

| | | | |
|---|---|---|---|
| 0 217 032 A3 | 4/1987 | European Pat. Off. | D04H 13/00 |
| 0 258 015 A2 | 3/1988 | European Pat. Off. | A44B 18/00 |
| 0 289 198 A1 | 11/1988 | European Pat. Off. | A44B 18/00 |
| 0 341 993 A1 | 11/1989 | European Pat. Off. | A44B 18/00 |
| 0 474 123 A1 | 3/1992 | European Pat. Off. | B32B 5/26 |
| 0 554 896 A1 | 8/1993 | European Pat. Off. | B32B 27/12 |
| 0 598 970 A1 | 6/1994 | European Pat. Off. | B26F 1/24 |
| 0 604 731 A1 | 7/1994 | European Pat. Off. | B32B 31/00 |
| 0 604 736 A3 | 7/1994 | European Pat. Off. | D01F 6/46 |
| 0604731 A1 | 7/1994 | European Pat. Off. | |
| 26 14 160 C3 | 10/1977 | Germany. | |
| WO 92/01401 | 2/1992 | WIPO. | |
| WO 94/19178 | 9/1994 | WIPO | B32B 5/26 |
| WO 95/16562 A1 | 6/1995 | WIPO | B32B 5/24 |

OTHER PUBLICATIONS

American Society for Testing and Material (ASTM) D 3822–95a, "Standard Test Method for Tensile Properties of Single Textile Fibers," pp. 138–147.

Patent Cooperation Treaty Search Report from the International Search Authority, International Application No. PCT/US 96/19849 dated Jul. 9, 1997.

Primary Examiner—James J. Bell
Attorney, Agent, or Firm—Brinks Hofer Gilson & Lione

[57] ABSTRACT

A laminate suitable for use as the hook component of a hook-and-loop fastener. The laminate comprises a first extensible substantially non-elastic layer and a second layer comprising a nonwoven material. The nonwoven material is prebonded by a number of first spaced-apart bond sites to form first bonded and first unbonded areas. The second layer is attached to the first layer by a plurality of second spaced-apart bond sites to form a bulked laminate having a plurality of second bonded and second unbonded areas. The second bonded and second unbonded areas together define a surface area of said bulked laminate with said second bonded areas covering from about 5 to about 20 percent of the surface area. At least 50 percent of the second bonded areas have an area of less than about 4 square millimeters and have a density of greater than about 2 bonds per square centimeter. The laminate is bulked due to said second layer having from about 15 to about 30 percent more surface area than the first layer per the same unit area of said laminate. Also disclosed are disposable absorbent articles including such a laminate.

44 Claims, 5 Drawing Sheets

U.S. PATENT DOCUMENTS

| | | | |
|---|---|---|---|
| 3,705,065 | 12/1972 | Stumpf | 156/72 |
| 3,708,361 | 1/1973 | Stumpf | 156/72 |
| 3,709,768 | 1/1973 | Stumpf | 161/63 |
| 3,720,554 | 3/1973 | Stumpf | 156/62.6 |
| 3,802,817 | 4/1974 | Matsuki et al. | 425/66 |
| 3,863,304 | 2/1975 | Brumlik | 24/204 |
| 3,922,455 | 11/1975 | Brumlik | 428/85 |
| 3,927,443 | 12/1975 | Brumlik | 24/204 |
| 4,041,203 | 8/1977 | Brock et al. | 428/157 |
| 4,214,582 | 7/1980 | Patel | 128/156 |
| 4,258,094 | 3/1981 | Benedyk | 428/85 |
| 4,297,404 | 10/1981 | Nguyen | 428/85 |
| 4,340,563 | 7/1982 | Appel et al. | 264/518 |
| 4,704,116 | 11/1987 | Enloe | 604/385 A |
| 4,720,415 | 1/1988 | Vander Wielen et al. | 428/152 |
| 4,725,473 | 2/1988 | Van Gompel et al. | 428/156 |
| 4,761,318 | 8/1988 | Ott et al. | 428/85 |
| 4,798,603 | 1/1989 | Meyer et al. | 604/378 |
| 4,846,815 | 7/1989 | Scripps | 604/391 |
| 4,854,984 | 8/1989 | Ball et al. | 156/73.5 |
| 4,869,724 | 9/1989 | Scripps | 604/389 |
| 4,910,062 | 3/1990 | Zinke et al. | 428/95 |
| 4,919,738 | 4/1990 | Ball et al. | 156/73.5 |
| 5,032,122 | 7/1991 | Noel et al. | 604/391 |
| 5,176,668 | 1/1993 | Bernardin | 604/368 |
| 5,176,672 | 1/1993 | Bruemmer et al. | 604/385.1 |
| 5,192,606 | 3/1993 | Proxmire et al. | 428/284 |
| 5,226,992 | 7/1993 | Morman | 156/62.4 |
| 5,256,231 | 10/1993 | Gorman et al. | 156/178 |
| 5,326,612 | 7/1994 | Goulait | 428/100 |
| 5,336,552 | 8/1994 | Strack et al. | 428/224 |
| 5,368,927 | 11/1994 | Lesca et al. | 428/288 |
| 5,369,853 | 12/1994 | Okawa et al. | 24/446 |
| 5,380,313 | 1/1995 | Goulait et al. | 604/391 |
| 5,399,174 | 3/1995 | Yeo et al. | 604/365 |
| 5,407,439 | 4/1995 | Goulait | 604/391 |
| 5,453,318 | 9/1995 | Giacobbe | 428/286 |
| 5,509,915 | 4/1996 | Hanson et al. | 604/378 |
| 5,656,111 | 8/1997 | Dilnik et al. | 156/66 |
| 5,660,666 | 8/1997 | Dilnik et al. | 156/259 |
| 5,669,900 | 9/1997 | Bullwinkel et al. | 604/391 |

LAMINATE MATERIAL

BACKGROUND OF THE INVENTION

The present invention relates to a laminate material. Specifically, the present invention relates to a laminate material suitable for use as the loop component of a hook-and-loop fastener.

DESCRIPTION OF THE RELATED ART

A wide variety of hook-and-loop fasteners are known to those skilled in the art. Typically, the hook-and-loop fasteners comprise a hook component adapted to releasably engage with a loop component. Such hook-and-loop fasteners generally operate by being designed so that some portion of the hook component can engage the loop component thereby causing the two components to be held together until such time as sufficient force is applied to separate the components by disengaging the hook component from the loop component.

Many of the loop components operate best when they comprise relatively large open loops which can be easily engaged by a hook. Such materials have typically been formed through a knitting, stitchbonding, or weaving process. Unfortunately, knit or woven loop components also tend to be relatively expensive. Accordingly, such loop components have not found widespread acceptance for use on disposable absorbent products.

Further, in those instances in which hook-and-loop fasteners have been employed on disposable absorbent products, it has generally been necessary to minimize the amount the hook component and loop component employed on such products in order to keep the costs of the hook-and-loop fasteners acceptable. In some instances it may be desirable to employ greater amounts of hook or loop components in order to assist use by the consumer. This could be accomplished by reducing the cost of the hook and loop components.

With respect to the loop components, one option of reducing costs is to move from the use of a knit or woven material to the use of a nonwoven material. Nonwoven materials are generally cheaper and easier to produce than woven or knit materials. Unfortunately, such nonwoven materials have, in the past, not consistently presented loops which are large and open enough to easily engage available hook components. Nonetheless, it is desirable to provide nonwoven loop components which function in a manner which renders them suitable for use on disposable absorbent products. It is to this goal that the present invention is directed.

SUMMARY OF THE INVENTION

In one aspect, the present invention is directed to a laminate. The laminate comprises a first substantially non-elastic extensible layer and a second layer. The second layer comprises a nonwoven material having a basis weight of from about 5 grams per square meter to about 60 grams per square meter. The nonwoven material is prebonded by a plurality of first spaced apart bond sites which form first bonded and first unbonded areas. The second layer is attached to the first layer by a plurality of second spaced apart bond sites to form a bulked laminate with a plurality of second bonded and unbonded areas. The second bonded and unbonded areas together define a surface area of the bulked laminate. The second bonded areas cover from about 5 to about 20 percent of the surface area, with at least about 50 percent of said second bonded areas having a size of less than about 4 square millimeters and a density of greater than about 2 bonds per square centimeter. The laminate is bulked due to the second layer having from about 15 to about 30 percent more surface area than the first layer per the same unit area of said laminate.

In a second aspect, the present invention is directed to a disposable absorbent article. The article comprises a liquid pervious topsheet, a laminate defining at least a portion of an outer surface of the article, an absorbent core located between the topsheet and the laminate and a mechanical fastener joined to said article for releasably engaging with said laminate. The laminate comprises a first substantially non-elastic, extensible layer and a second layer. The second layer comprises a nonwoven material having a basis weight of from about 5 grams per square meter to about 60 grams per square meter. The nonwoven material is prebonded by a plurality of first spaced apart bond sites which form first bonded and first unbonded areas. The second layer is attached to the first layer by a plurality of second spaced apart bond sites to form a bulked laminate with a plurality of second bonded and unbonded areas. The second bonded and second unbonded areas together define a surface area of the bulked laminate. The second bonded areas cover from about 5 to about 20 percent of the surface area with at least about 50 percent of the second bonded areas have a size of less than about 4 square millimeters and a density of greater than about 2 bonds per square centimeter. The laminate is bulked due to the fact that the second layer has from about 15 to about 30 percent more surface area than said first layer per the same unit area of said laminate.

DETAILED DESCRIPTION OF THE PREFERRED EMBODIMENT

Figure 1:
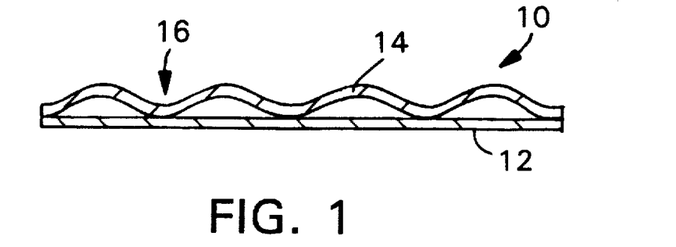
FIG. 1 is a cross-sectional side view of a laminate according to the present invention.

The present invention relates to a laminate material comprising a first substantially non-elastic layer and a second layer. As used herein, reference to the term "layer" can be meant to include a single piece or sheet of material as well as a laminate made from a plurality of individual sheets of material. With reference to FIG. 1, a laminate 10 according to the present invention is illustrated comprising a first substantially non-elastic extensible layer 12 and a second layer 14. The first layer 12 and second layer 14 are thermally bonded together at locations 16.

The first layer 12 is substantially non-elastic. As used herein, a material will be considered to be non-elastic when it is capable of being stretched in at least one direction by at least 25 percent, preferably at least 100 percent and, upon release of the force causing the stretching, retracts from about 15 to about 30 percent, wherein the percent stretch and percent retraction are calculated according to the following formulas:

$$\frac{L_2 - L_1}{L_1} \times 100 = \text{percent stretch}$$

$$\frac{L_2 - L_3}{L_2} \times 100 = \text{percent retraction}$$

Wherein $L_1$ is the length of the first substrate prior to stretching, $L_2$ is the length of the first substrate after stretching but before release of the force causing the stretching, and $L_3$ is the length of the first substrate after release of the force causing the stretching.

Materials suitable for use as the first substantially nonelastic extensible, layer includes materials such as films, nonwoven materials, woven materials, knits, scrims, and tissues.

The films can be made of breathable or nonbreathable materials. In addition, the films can be apertured. In forming the films, the films may be coextruded to increase bonding and the films may be filled with an opacifying agent such as titanium dioxide. The nonwoven materials can be made from longer, more continuous fibers such as spunbond and meltblown fibers or from shorter staple fibers such as are used in bonded carded webs. Suitable fibers include natural and synthetic fibers as well as bicomponent and multicomponent/polymer fibers. The nonwoven webs may be hydroentangled and they can be formed using any number of techniques including spunbonding, meltblowing, solution spinning, and wet laying. In addition, laminated layers such as spunbond/meltblown/spunbond composites can be used for the first layer. The woven and knit materials can be made from both synthetic and natural fibers. They can also be made from combinations of both natural and synthetic fibers. Tissue-based layers are typically made from natural fibers such as pulp, but they can also include synthetic fibers. As used herein, the term "extensible" refers to a material which is capable of being stretched from a first or original length $L_1$ to a second and greater length $L_2$ and then, upon release of the stretching forces, the material retracts to a third length $L_3$ which is less than the second length $L_2$ but greater than the first length $L_1$. In one preferred embodiment of the present invention, the first layer is a polyolefin film, suitably polypropylene, having a thickness of about 0.015 millimeter. The polypropylene film can suitably be made from a Himont catalloy polypropylene resin available from Himont U.S.A., Inc., of Wilmington, Del.

The second material comprises a nonwoven material. The nonwoven material can be made from longer, more continuous fibers such as spunbond and meltblown fibers or from shorter staple fibers such as are used in bonded carded webs. The fibers suitably have a denier of from about 1.5 to about 10, alternatively of from about 2 to about 6. Suitable fibers include natural and synthetic fibers as well as bicomponent and multicomponent/polymer fibers. The nonwoven materials may be hydroentangled and they can be formed using any technique including spunbonding, meltblowing, solution spinning and wet laying. In addition, laminated layers such as spunbond/meltblown/spunbond composites can be used for the second layer. The nonwoven material has a basis weight of from about 5 grams per square meter to about 60 grams per square meter, alternatively of from about 15 grams per square meter to about 30 grams per square meter.

In order to provide the nonwoven material with sufficient internal strength to allow it to be handled and for the laminate of the present invention to function as the loop component of a hook-and-loop fastener, the nonwoven material is prebonded by a plurality of first spaced apart bond sites to form first bonded and first unbonded areas. The first bonded areas provide structural integrity to the nonwoven web and serve to bond the fibers of the nonwoven web together, thereby decreasing the tendency of the fibers of the nonwoven webs to pull apart as individual fibers during use of the laminate of the present invention as the loop component of a hook-and-loop fastener (during disengagement).

In one preferred embodiment, the first spaced apart bond sites are formed by the application of thermal energy. For example, the nonwoven material may be subjected to an embossing pattern on heated rolls to thermally fuse the fibers of the nonwoven material together. Alternatively, particulate bonding agents may be incorporated into the web and heated to a temperature sufficient to cause the bonding agents to become activated and bond the fibers of the nonwoven material together. Other methods of forming the first spaced apart bond sites include ultrasonic bonding or adhesive bonding or combinations of one or more methods. If bicomponent fibers are used in forming the nonwoven material, the first spaced apart bond sites may be formed by through air bonding.

Applicants have discovered that it is generally desired to have the first bonded areas be discrete areas having a size of from about 0.3 to about 2.0 square millimeters, alternatively of from about 0.5 to about 1.0 square millimeter. The first bonded and first unbonded areas together define a planar surface area of the nonwoven material. The bonded areas suitably comprise from about 3 to about 35, alternatively of from about 5 to about 15 percent of the planar surface area of the nonwoven material.

In one specific embodiment, at least 50 percent of the first bonded areas are discrete areas having a size of from about 0.5 to about 0.8 millimeter, alternatively about 90 percent of the first bonded areas are discrete areas having a size of from about 0.5 to about 0.8 millimeters.

As a general rule, Applicants have discovered that a generally uniform pattern of discrete first bonded areas and first unbonded areas is desired. Further, in one specific embodiment, the first bonded areas have a size of from about 0.5 to about 0.8 square centimeters, cover approximately 5 to about 15 percent of the surface area of the nonwoven material and have a density of from about 5 to about 20 first bonded areas per square centimeter of surface area of the nonwoven material.

Figure 2:
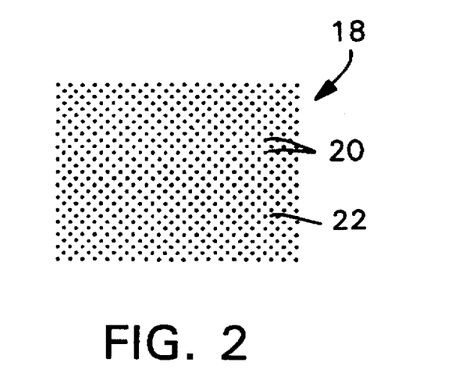
FIG. 2 is a schematic illustration of a bonding pattern suitable for use on the nonwoven second layer of the laminate according to the present invention.

FIG. 2 illustrates a preferred bonding pattern suitable for use in forming the prebonded nonwoven material. With reference to FIG. 2, the nonwoven material 18 comprises first bonded areas 20 and first unbonded areas 22. The first bonded areas 20 are uniform in size and have a size of 0.68 square millimeters, cover about 10.6 percent of the surface area of the nonwoven material, thus having a density of 15.5 first bonded areas per square centimeter of the nonwoven material.

Optical imaging can be used to determine the size of the first bonded areas and to calculate the percent of the surface area of the nonwoven material which the first bonded areas comprise. Alternatively, when the first bonded areas are formed by passing the nonwoven material through an embossing roll, the embossing pattern can be used to calculate the size of the first bonded areas (land size) and the percent of the surface area of the nonwoven material which the bonded areas comprise. When the first bonded areas are formed through the use, for example, of a particulate bonding agent, the size of the bonded areas and the surface area which the bonded areas comprise can be determined by optical imaging in which, for example, it may be desirable to stain the bonding agent to enhance the contrast between the bonding agent and the fibers. Any method suitable for prebonding the nonwoven material is believed suitable for use in the present invention.

The second layer is attached to the first layer with a plurality of second spaced-apart bond sites to form a bulked laminate. The laminate is a bulked laminate because the second layer has from about 15 to about 30 percent more surface area than said first layer per the same unit area of said laminate. This is suitably achieved by stretching the first layer from a first or original length $L_1$ to a second length $L_2$ which is greater than the original length ($L_1$). After the first layer has been stretched, while it is still in a stretched condition, the second layer is attached to the first layer. As described above, the first layer has the ability to recover a portion of its stretched length. As a result, after the first and second layers have been attached to one another, the stretching forces are released and the first layer retracts slightly to a third length $L_3$ which is greater than the first or original length $L_1$ of the first layer yet slightly less than the second stretched length ($L_2$) of the first layer. Due to the slight recovery of the first layer, the second layer tends to gather and form pillows, thereby imparting a bulky, more three-dimensional appearance to the composite. Specifically, this results in a second layer having a larger surface area than the first layer per the same unit area of the composite. Specifically, if the first layer has 15 percent retraction (calculated as described herein), the second layer will have 15 percent more surface area than said first layer per same unit area of said laminate.

The second bond sites attaching the second layer to the first layer form a plurality of second bonded and second unbonded areas. The second bonded and second unbonded areas together define a surface area of the laminate. The second bonded areas cover from about 5 to about 20 percent, alternatively of from about 8 to about 12 percent of the surface area of the laminate. At least about 50 percent, alternatively at least about 75 percent of the second bonded areas have a size of less than about 4 square millimeters, alternatively of less than about 2 square millimeters, alternatively of from about 0.5 to about 1.5 square millimeters. In one embodiment, at least about 90 percent of said second bonded areas have a size of less than about 4 square millimeters, alternatively of less than about 2 square millimeters, alternatively of from about 0.5 to about 1.5 square millimeters. The second bonded areas suitably have a density of greater than about 2 bonds per square centimeter, alternatively of greater than about 5 bonds per square centimeter.

When the laminate materials of the present invention are intended to be used as the loop component of a hook-and-loop fastener, Applicants have found that it is generally desirable to use a relatively large number of small bonding points to bond the first and second layers together. That is, the second bonded areas are small and numerous. Further, it is generally desired that the second bonded areas be discrete and relatively uniformly located over the surface of the laminate. In one specific embodiment the second bonded areas have a size of from about 0.5 to about 1.5 square millimeters, cover approximately 7 to about 10 percent of the surface area of the laminate and have a density of from about 7 to about 10 second bonded areas per square centimeter of surface are of the laminate.

Further, when the laminate materials of the present invention are intended to be used as the loop component of a hook-and-loop fastener, it is desirable that the embossing roll used to form the second bonded areas have a pin depth which allows for the formation of relatively open second unbonded areas. In one embodiment, the embossing roll used to form the second bonded areas has a pin depth of at least about 1.3 millimeters, alternatively of from about 1.3 millimeters to about 1.7 millimeters. Those skilled in the art will recognize that higher pin depths can result in an unacceptable amount of pin breakage. Lower pin depths may unacceptably compress the second unbonded areas. Those skilled in the are will be able to balance these two factors in choosing an acceptable pin depth.

Figure 3:
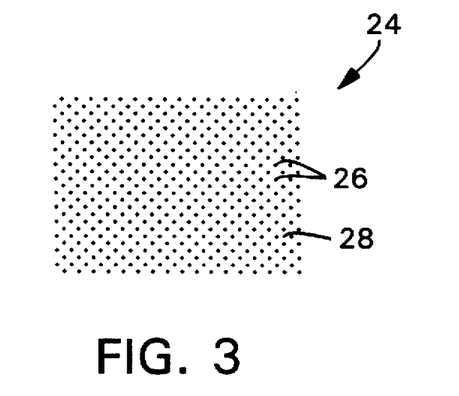
FIG. 3 is a schematic illustration of a bonding pattern suitable for use in forming the laminate of the present invention.

With reference to FIG. 3, a suitable bonding pattern for bonding the first and second layers together is illustrated. Laminate 24 includes second bonded areas 26 and second unbonded areas 28. The second bonded areas 26 are uniform, have a size of about 1.0 square millimeter, and cover about 8.0 percent of the surface area of the laminate material, thus having a density of 8.0 second bonded areas per square centimeter of laminate material.

The first and second layers may be thermally bonded to one another, adhesively bonded to one another, sonically bonded to one another, bonded to one another by a combination of two or more bonding methods, or generally by any bonding method known to those skilled in the art. When using adhesives, the adhesives may be water-based, solvent-based, pressure-sensitive, or hot melt adhesives and may be printed in any desireable pattern. In one specific embodiment, the first and second layers are thermally bonded to one another by embossing at an elevated temperature.

When the first layer comprises a film, and it is desired that the film maintain its integrity to provide a liquid barrier, it may be desirable to select a second layer formed from materials which have an onset of melting point (as determined by, for example, differential scanning calorimetry) lower than the onset of melting point of the film. This may allow better bonding between the second layer and the first layer without fear of damaging the integrity of the first film layer. The bonding between the second layer and the first layer will also be affected by the relative abilities of the materials to conduct thermal energy. The bonding temperature and melting curve of the film and second layer can be optimized to provide strong bond points to prevent fiber stringout of the second layer or delamination and yet maintain the liquid barrier properties of the film layer. The ability to minimize fiber stringout and delamination allows for the use of nonwoven materials in forming the laminates of the present invention and in allowing use of the laminates as the loop component of a hook-and-loop fastener.

Once the first layer has been bonded to the second layer, and the composite has relaxed (stretching forces released), the newly formed laminate cannot be capable of stretching more than about 25 percent of the composite's relaxed length $L_3$ without affecting the lamination or bonding of the first layer to the second layer.

Figure 4:
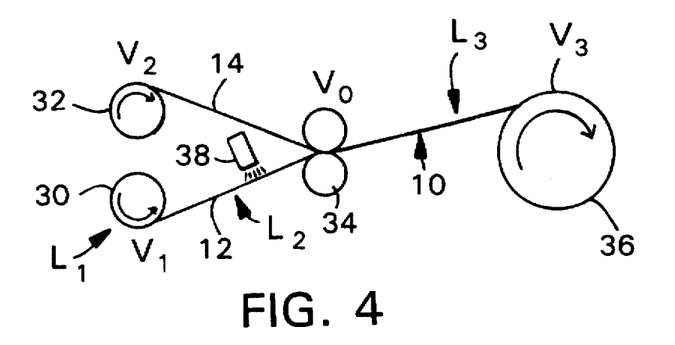
FIG. 4 is a schematic view of a first process for forming the laminate of the present invention.
Figure 5:
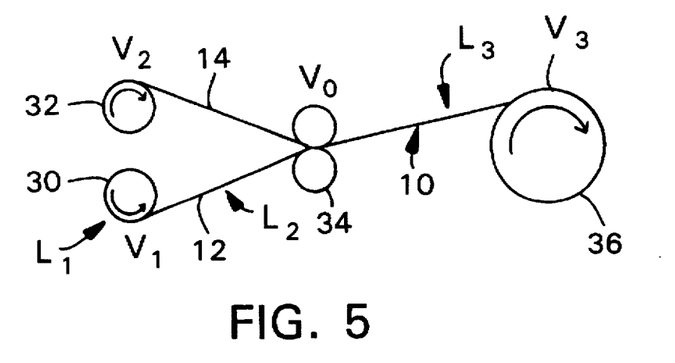
FIG. 5 is a schematic view of a second process for forming the laminate of the present invention.

The process of forming the laminate 10 of the present invention is shown in schematic form in FIGS. 4 and 5 of the drawings. For purposes of illustration only, the first substantially non-elastic layer 12 is described as being a thermoplastic film such as a polypropylene film and the second layer 14 is a layer of nonwoven spunbonded material made from extruded polypropylene fibers. The material of the first layer 12 is shown as being unwound from a supply roll 30. It is also possible when using films in the process to extrude the film in line as part of the process. The second layer 14 as shown in FIGS. 4 and 5 is unwound from a second supply roll 32 and, along with the first layer 12, is sent through a bonder 34. To create stretch in the first layer 12, the first supply roll 30 is driven or retarded at a first speed $V_1$ and a second supply roll 32 is driven at a second speed $V_2$ while the takeup roll 36 is driven or retarded at a third speed $V_3$. At the point of bonding at the bonder 34, the first layer 12 and the second layer 14 have a common speed $V_0$. Prior to the bonder 34, the speed $V_2$ of the second layer 14 can be less than or equal to $V_0$, but in either event, $V_1$ is less than $V_2$. By running the first supply roll 30 at a slower rate than the second supply roll 32, there is a stretch imparted to the first layer 12 such that the film of first layer 12 is stretched at least 25 percent beyond its first original length. While the first layer 12 is in its stretched state, the second layer 14 is bonded to the first layer 12.

In FIG. 4, the first and second layers 12 and 14 are shown as being bonded to one another through the use of adhesives and pressure via bonder equipment 34, including a smooth anvil roll and a pattern roll, and an adhesive sprayer 38, both of which are well known to those of ordinary skill in the art. Alternatively, as shown in FIG. 5, the adhesive sprayer 38 may be deleted in which case it is desirable to apply heat to one or both of the bonding rolls of bonder 34. The bonder 34 serves to bond the two layers to one another across the width of the material in the cross-machine direction. By selecting the bond pattern on the pattern roll, the location of thermal bonding 16 can be spaced at regular or irregular distances from one another along the material in the machine direction so that there are a plurality of bonded and unbonded sites along the length of the material as shown in FIGS. 1 and 3.

Applicants have discovered that it is generally desirable that the first and second bonded areas be discrete areas having a given size as opposed to continuous lines or patterns of lines. This is believed to be because of the ability to get uniform bonding with discrete area while minimizing the overall bond area.

Once the first and second layers 12 and 14 have been bonded to one another, the laminate 10 is wound around a take-up roll 36 which is traveling at a speed $V_3$ which is less than the speed $V_2$ of the second supply roll 32. As a result, the laminate material 10 can relax from the stretched state between the supply rolls 30 and 32 and the bonder 34 to a relaxed condition beyond the bonder 34 so that the laminate material 10 can be wound on take-up roll 36.

As the laminate material 10 relaxes between the bonder 34 and the take-up roll 36, the first layer retracts from between about 15 and about 30 percent of the expanded length between the first supply roll 32 and the bonder 34, thereby causing the second layer 14 to gather up or pillow as shown in FIG. 1 to create a three-dimensional structure. Alternatively, the take-up roll 36 can be driven at the same speed as the bonder 34 in which case the laminate material 10 will be wound up while still in a stretched state. In this case, the laminate 10 will retract slightly while on roll 36 and the remainder of the retraction will be achieved as the laminate 10 is unwound from the roll 36. When using film as the first layer, the first layer may be stretched to many times its original length, in fact as much as 1200 percent or more. During such stretching, the film will usually permanently deform. Referring to FIGS. 4 and 5, while on the supply roll 30, the first layer 12 has a first length $L_1$. Due to the differential speed between the first supply roll 30 and the bonder 34, first layer 12 is stretched to a second length $L_2$ with $L_2$ being greater than $L_1$. Depending on the particular material being used for first layer 12, the degree of stretching necessary to permanently deform first layer 12 may be as little as 25 percent to as high as 1200 percent, especially when using various plastic films as the first layer 12. In any event, however, it should be remembered that in extending the first layer from $L_1$ to $L_2$, it is sometimes desirable that the material of first layer 12 be permanently deformed so that upon relaxation after the bonder 34, the relaxed length $L_3$ is slightly less than the stretched length $L_2$ but much greater than the original or first length $L_1$ due to the permanent deformation of the material during the stretching process.

In FIGS. 4 and 5 of the drawings, the laminate 10 of the present invention is shown as being made into a two ply laminate with stretch and relaxation being imparted in only one direction (the machine direction). With the equipment available today, it is also possible to stretch the first layer 12 in two or more directions which may be offset with respect to one another at any desired angle including right angles and angles greater than or less than 90 degrees. Besides stretching the first layer 12, the second layer 14 can also be stretched before the two layers are laminated together. It is desirable, however, that the degree of extension or stretching of the second layer 14 be less than that of the first layer 12. Of course, even if the second layer is stretched, the first layer retracts to a greater extent than the second layer. The stretching of the second layer 14 can be substantially parallel to the direction of extension of the first layer 12 where it can be non-parallel or even perpendicular to the direction of extension of the first layer 12.

It is also possible to create multilayered laminates. As explained earlier, second layer 14 may itself be made from a laminate of several layers such as a composite of spunbond/meltblown/spunbond materials bonded to one another prior to the composite being bonded to the first layer 12. The same is true with respect to the first layer 12. Alternative methods of forming the laminates of the present invention are disclosed, for example, in U.S. patent application Ser. No. 08/483,627 filed on Jun. 7, 1995, in the name of McCormack et al. U.S. Pat. No. 5,226,992 issued Jul. 13, 1993, to Morman and European Patent Application Number EP 0 110 010 published Apr. 8, 1987, listing the inventors as Taylor et al.

When the second layer is formed from meltblown or spunbond polyolefin fibers, it is generally desired that the fibers have a peak elongation of less than about 300 percent, alternatively of less than about 200 percent, alternatively of less than about 150 percent as determined by American Society of Testing and Materials (ASTM) test method D-3822. The inventors have discovered that improved performance can be obtained with materials having lower peak elongation.

Figure 6:
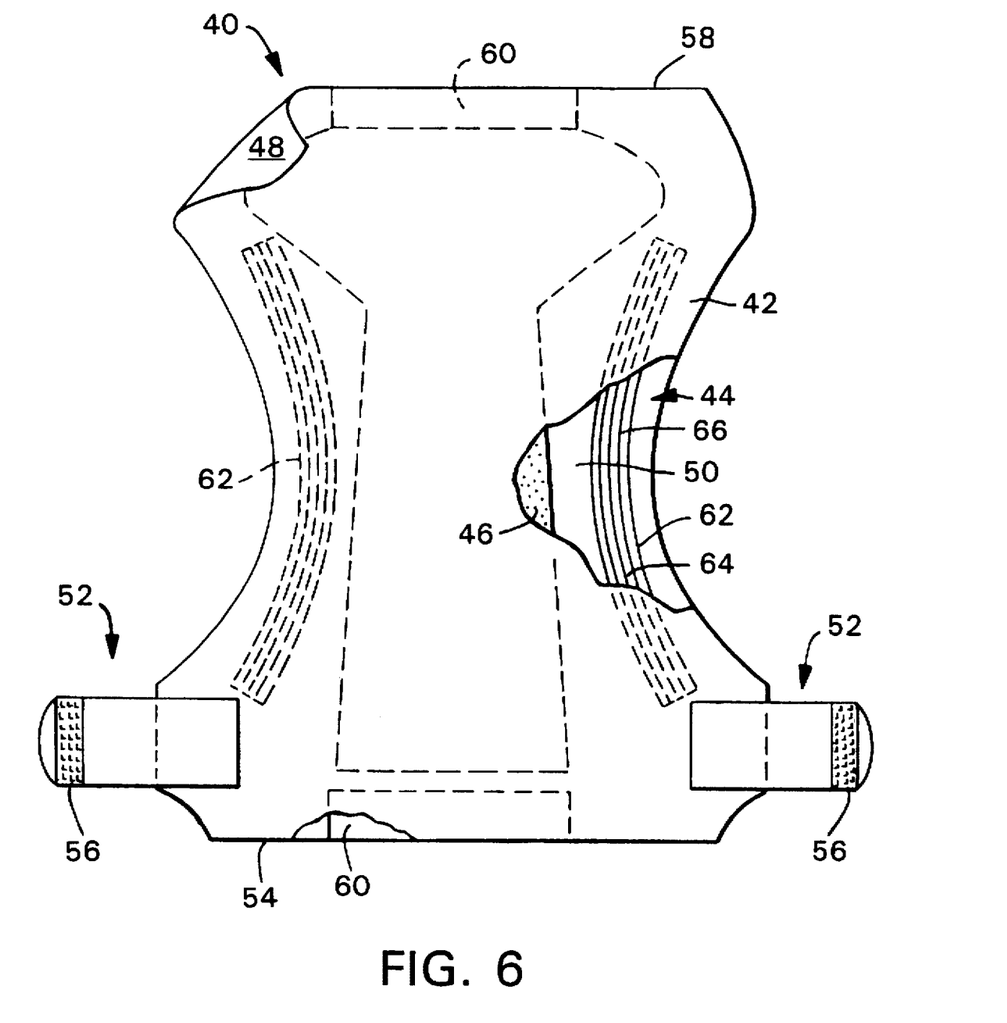
FIG. 6 is a planar view of a disposable absorbent diaper according to the present invention.

The laminates of the present invention are suited for use as the loop components of hook-and-loop fasteners. Such loop components may be employed in any situation in which hook and loop fasteners have been employed. Examples of such uses include clothing and disposable absorbent articles. In one particular embodiment of the present invention, the laminate material of the present invention is employed on a disposable absorbent article. With reference to FIG. 6, disposable diaper 40 is illustrated. Disposable diaper 40 includes a liquid-pervious topsheet 42, a laminate 44 according to the present invention and an absorbent core 46 located between the topsheet 42 and the laminate 44. The laminate 44 defines at least a portion of the outer surface of the diaper 40. Specifically, the second layer 48 forms the outer surface of the diaper 40.

The first layer 50 is located towards the body of a wearer in use. In this specific embodiment, it is often desired that the first layer comprise a film so as to render the laminate liquid impervious. The diaper further includes fastening tabs 52 located on a first longitudinal end 54 of diaper 40. The fastening tab 52 includes hook components 56 which are adapted to releasably engage with the second layer 48 of laminate 44. The diaper 40, thus provided, can be fastened about the body of a wearer through the use of fastening tabs 52. The hook components 56 can engage the second layer 48 at any location on the outer surface of diaper 40. This offers convenience to the consumer and the flexibility to ensure a proper fit about the body of a wearer.

In the past, diapers which employed hook-and-loop fasteners often included a separate patch of loop component in the second longitudinal end 58 of a diaper to which the hook components were intended to be engaged. The separate patch of loop component was the only location to which the hook components were intended to engage to fasten the diaper about the waist of a wearer. This added expense to the diaper and limited the locations to which the hook components 56 could be releasably engaged. By having the entire outer surface of diaper 40 comprise the second layer 48, the consumer can engage hook components 56 at any location on the outer surface of the diaper 40.

The diaper 40 further includes waist elastics 60 and leg elastics 62. Leg elastics 62 include carrier sheet 64 and elastic strands 66.

The specific construction and other alternative constructions of diaper 40 as well as the materials suitable for use in forming diaper 40 are known to those skilled in the art and can be seen from reference to the following U.S. patents and patent applications, all of which are hereby incorporated by reference: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; U.S. patent application Ser. No. 08/096,654 filed Jul. 22, 1993, in the name of Hanson et al., issued Apr. 23, 1996, as U.S. Pat. No. 5,509,915, and U.S. patent application Ser. No. 08/263,281 filed Jun. 21, 1994, in the name of Dilnik et al., and now abandoned in favor of continuing applications, see Dilnik et al. U.S. Pat. Nos. 5,656,111, issued Aug. 12, 1997, and 5,660,666, issued Aug. 26, 1997.

Applicants have found that hook components having hooks which are small and have a relatively small hook return are particularly well suited for use in the present invention. Specifically, it is often desired that the hooks have a height of less than about 0.4 millimeter and a hook return of less than about 0.13 millimeter. Such hook components are commercially available from the Minnesota Mining and Manufacturing Company under the trade designation CS-200 and from VELCRO® Group Corporation under the trade designation CFM-29.

Test Methods
Shear Test
Equipment and Materials

1. A Sintech System 2 or equivalent tensile tester with a computerized data acquisition system. The Sintech System 2 can be obtained from Sintech, Inc., Research Triangle Park, N.C.

2. A handheld roller weighing 4.5 pounds which can be attained from Chemsultants International, Mentor, Ohio.

3. A clipboard and additional removable clip (IDL Model No. 11240).

Test Procedure

1. A 2.25×7 inch sample of the loop material to be tested is secured to the chasis of a diaper commercially available from the Kimberly-Clark Corporation under the trade designation HUGGIES® Supreme. The loop material is secured to the chasis of the diaper in the same area as the loop material on the commercially available diaper. The loop material is then cut from the diaper by cutting across the width of the diaper approximately 1 inch below (toward the rear of the diaper) the bottom of the loop patch. The portion of the diaper chasis including the loop material is then clamped to the clipboard between the two clips of the clipboard. The loop material is facing up.

2. A 0.5×1.75 inch sample of the hook material is attached to the fastening tab of the HUGGIES® Supreme diaper referenced above in the same location as the hook material on the commercially available diaper. The entire fastening tab is removed from the diaper by cutting. The fastening tab is placed on top of the loop material between the two clips such that the 1.75 inch dimension of the hook material is approximately centered on the 2.25 inch dimension of the loop material. The specimen (hook in place on loop) is rolled down with the 4.5 pound roller for five cycles (one cycle=a pass over the sample and the return pass). The hook-and-loop composite is removed from the clipboard. One end of the loop material is clamped in the lower jaw of the tensile tester and the end of the fastening tab opposite said end of the loop material is fastened in the upper jaw.

The following settings are used for the tensile tester during testing.

| | |
| --- | --- |
| Crosshead speed: | 250 ± 10 milliliters per minute |
| Chart speed: | 500 ± 10 millimeters per minute |
| Gauge length: | 38 ± 1 millimeter |
| Test units: | grams |
| Break sensitivity: | 95 percent |

3. The test is initiated by setting the crosshead in motion. At the end of the test, the crosshead is returned. The peak load value in grams is recorded. This peak load (shear strength) is reported in grams.

EXAMPLES

A laminate material according to the present invention was formed using the process generally described in FIG. 5. The laminate was formed using a polypropylene film commercially available from Consolidated Thermoplastics under the trade designation XBPP-133. The film had a thickness of 0.015 millimeter. The second layer was a 0.7 ounce per square yard (24 grams per square meter) spunbond layer formed from a mixture of 80 weight percent polypropylene commercially available from Exxon Chemical Company under the trade designation 3445 and 20 weight percent Catalloy™ KSO84 commercially available from Montell USA. The spunbond fibers had a denier of about 2.5 and were thermally prebonded with a uniform dot pattern so as to provide bonded areas covering about 10.6 percent of the surface of the spunbond material. The first bonded areas had a size of about 0.68 square millimeters and were formed by passing the spunbond material through embossing rolls at a temperature of about 315° F.

The film and nonwoven material were subjected to a thermal bonding process as shown in FIG. 5. Referring to Table 1, the polypropylene film was driven at a speed $V_1$ of 25 feet per minute. The spunbond material was traveling at a speed $V_2$ of 50 feet per minute, and at the point of lamination, the composite was traveling at a speed $V_0$ of 50 feet per minute. On the take-up roll, the laminate was being taken up at a speed $V_3$ of 38 feet per minute. The film was stretched 100 percent beyond its original or first length L1 before the spunbond material was bonded to the film. The stretched length corresponded to the second length $L_2$ discussed above. After the bonding process, the film/nonwoven laminate was allowed to retract from its second length $L_2$ to a third length $L_3$. Referring again to Table 1, the laminate had a percent retraction of 24 percent. The second bonded areas were formed by passing the spunbond material through embossing rolls in which the anvil roll had a temperature of 232° F., the pattern roll had a temperature of 300° F., and the rolls exerted a nip pressure of 30 pounds per square inch.

TABLE 1

| First Layer: | 0.015 millimeter polypropylene film | $V_1 = 25$ |
|---|---|---|
| Second layer: | 2.4 gsm pp/catalloy SB 10.6% thermally prebonded | $V_2 = 50$ |
| Lamination: | Thermally point bonded | $V_0 = 50$ |
| Process Conditions: | Pattern Roll temperature 300° F. Anvil Roll Temperature 232° F. Nip Pressure 30 psi | |

% stretch: $\frac{50-25}{25} \times 100 = 100\%$

% retraction: $\frac{50-38}{50} \times 100 = 24\%$

A variety of laminates were formed by the above process using pattern rolls which differed in pin size and density to provide different levels of bond areas. Additionally, the pin pattern was varied to evaluate the effect of pattern on performance. The following samples were prepared.

TABLE 2

| Sample | Pin Size[1] | Pin Density[2] | Pattern[3] | % Bond Area |
|---|---|---|---|---|
| A | 0.00096 (0.0062) | 53 (8.22) | A | 5.1 |
| B | 0.00096 (0.0062) | 80 (12.4) | A | 7.7 |
| C | 0.00096 (0.0062) | 160 (24.8) | A | 15.4 |
| D | 0.0016 (0.010) | 53 (8.22) | A | 8.5 |
| E | 0.0016 (0.010) | 80 (12.4) | A | 12.8 |
| F | 0.0016 (0.010) | 27 (4.19) | A | 4.3 |
| G | 0.0016 (0.010) | 53 (8.22) | C | 8.5 |
| H | 0.0016 (0.010) | 53 (8.22) | B | 8.5 |
| I | 0.0036 (0.023) | 80 (12.4) | A | 28.8 |
| J | 0.0036 (0.023) | 53 (8.22) | A | 19.1 |

Figure 7:
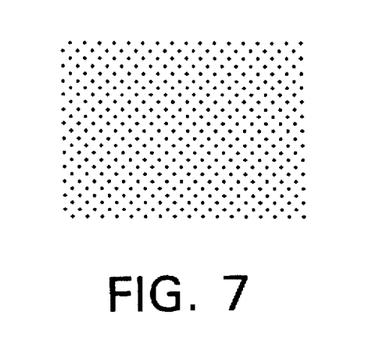
FIGS. 7–9 illustrate bonding patterns used in connection with the examples.
Figure 8:
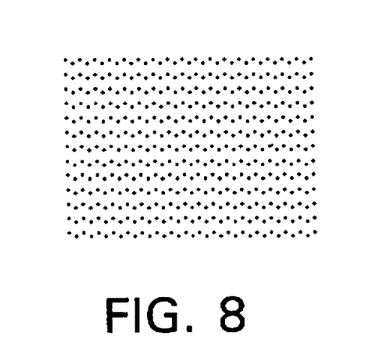
Figure 9:
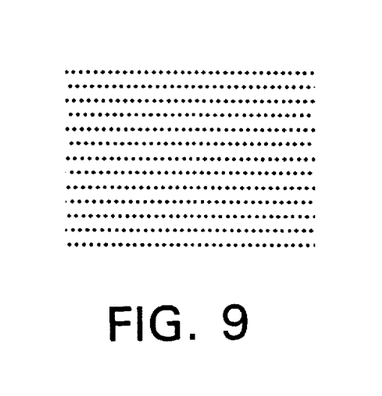

[1]All pins are square - listed value in square inches, and (square centimeters)
[2]Pins per square inch and (pins per square centimeter)
[3]Pattern A = FIG. 7
Pattern B = FIG. 8
Pattern C = FIG. 9

The laminate materials described in Table 2 were tested to determine their shear value. For all testing, the hook material used was a hook material available from VELCRO® Group Corporation under the trade designation CFM-29-1003. The results of this testing are set forth in Table 3 and graphically illustrated in FIG. 10.

TABLE 3

| Sample | Shear[1] |
|---|---|
| A | 2296 |
| B | 2844 |
| C | 2980 |
| D | 3149 |

TABLE 3-continued

| Sample | Shear[1] |
|---|---|
| E | 3188 |
| F | 1875 |
| G | 2790 |
| H | 2721 |
| I | 2435 |
| J | 3279 |

[1]In grams shear per square inch; hook material CFM-29-1003 for all samples tested.

Figure 10:
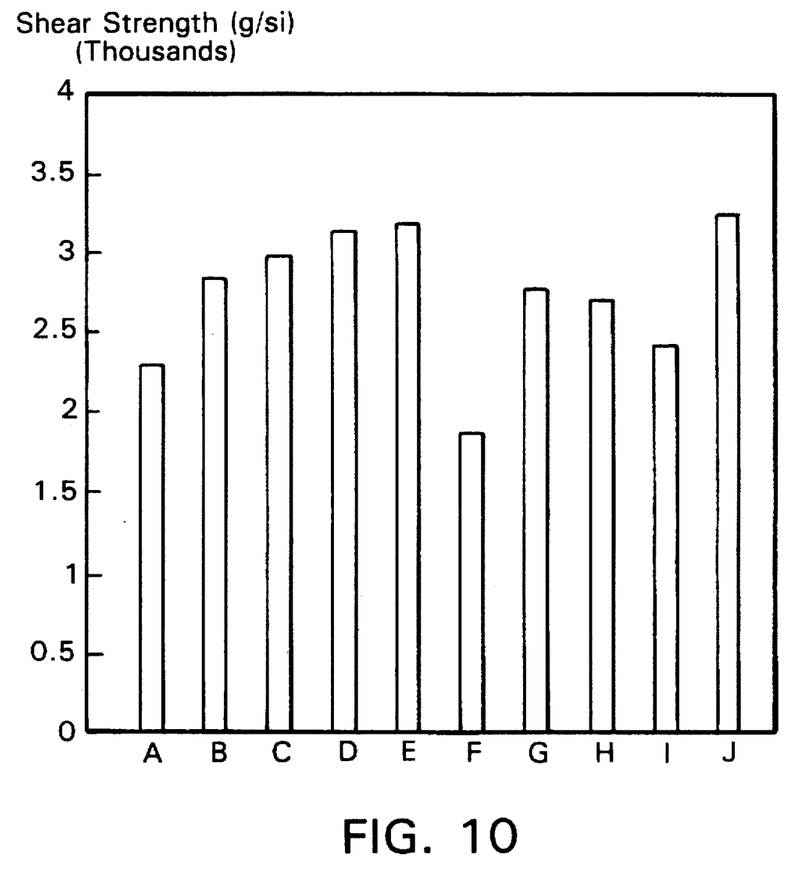
FIG. 10 graphically illustrates the data set forth in Table 3.

As can be seen from reference to Table 2, Table 3 and FIG. 10, within the 8–20 percent bond area, little variation was seen in the shear strength between test samples. A low percent bond area (Samples A and F) produced a laminate having relatively low shear strength due to the fiber pullout and delamination. A high percent bond area (Sample I) presented relatively low shear strength due to insufficient hook penetration. Samples G and H having a non-uniform bond patterns also exhibited lower shear performance.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A laminate comprising:
   a first substantially non-elastic, extensible layer, and
   a second layer, said second layer comprising a nonwoven material having a basis weight of from about 5 grams per square meter to about 60 grams per square meter, and being prebonded by a plurality of first spaced-apart bond sites to form first bonded and first unbonded areas, said second layer being attached to said first layer with a plurality of second spaced-apart bond sites to form a bulked laminate with a plurality of second bonded and second unbonded areas, said second bonded and second unbonded areas together defining a surface area of said bulked laminate, said second bonded areas covering from about 8 to about 20 percent of said surface area, at least 50 percent of said second bonded areas having a size of less than about 4 square millimeters and having a density of greater than about 2 bonds per square centimeter, said laminate being bulked due to said second layer having from about 15 to about 30 percent more surface area than said first layer per the same unit area of said laminate.

2. The laminate according to claim 1 wherein said first layer comprises a polyolefin film.

3. The laminate according to claim 1 wherein said second layer is a nonwoven material formed from spunbond fibers.

4. The laminate according to claim 3 wherein said spunbond fibers comprise a polyolefin material and have a thickness of about 2.5 denier per filament.

5. The laminate according to claim 3 wherein said spunbond fibers have a peak elongation of less than about 300 percent.

6. The laminate according to claim 5 wherein said spunbond fibers have a peak elongation of less than about 200 percent.

7. The laminate according to claim 1 wherein said first spaced apart bond sites are formed by the application of thermal energy.

8. The laminate according to claim 7 wherein said first spaced apart bond sites cover from about 3 to about 35 percent of a surface area of said second layer.

9. The laminate according to claim 8 wherein said first spaced apart bond sites cover from about 5 to about 15 percent of said surface area of said second layer.

10. The laminate according to claim 8 wherein said first bonded areas have a size of from about 0.3 square millimeters to about 2.0 millimeters.

11. The laminate according to claim 10 wherein said first bonded areas have a size of from about 0.5 square millimeter to about 1.0 square millimeter.

12. The laminate according to claim 8 wherein at least about 50 percent of said first bonded areas have a size of from about 0.5 square millimeter to about 0.8 square millimeter.

13. The laminate according to claim 12 wherein at least 90 percent of said first bonded areas have a size of from about 0.5 square millimeter to about 0.8 square millimeter.

14. A laminate according to claim 10, 11, 12, or 13 wherein said first bonded areas have a bond density of from about 5 to about 20 bonds per square centimeters.

15. The laminate according to claim 1 wherein at least about 75 percent of said second bonded areas have a size of less than about 4 square centimeters.

16. The laminate according to claim 1 wherein at least about 90 percent of said second bonded areas have a size of less than about 4 square millimeters.

17. The laminate according to claim 14 wherein said second bonded areas have a size of less than about 2 square millimeters.

18. The laminate according to claim 1 wherein said second bonded areas have a size of less than about 2 square millimeters and a density of from about 7 to about 10 bonds per square centimeter.

19. The laminate according to claim 1, 15, 16, or 18 wherein said second bonded areas are generally uniformly spaced from one another.

20. The laminate according to claim 1 wherein said first layer is a polyolefin film and said second layer is a nonwoven material formed from spunbond fibers and the temperature at which the onset of melting of said first layer occurs is greater than the temperature at which the onset of melting of said second layer occurs.

21. The laminate according to claim 1 wherein said laminate is water impervious.

22. A laminate comprising:
a first substantially non-elastic, extensible layer, and
a second layer, said second layer comprising a nonwoven material having a basis weight of from about 15 grams per square meter to about 30 grams per square meter, and being prebonded by a plurality of first spaced-apart bond sites to form first bonded and first unbonded areas, said second layer being attached to said first layer with a plurality of second spaced-apart bond sites to form a bulked laminate with a plurality of second bonded and second unbonded areas, said second bonded and second unbonded areas together defining a surface area of said bulked laminate, said second bonded areas covering from about 8 to about 20 percent of said surface area, at least 90 percent of said second bonded areas having a size of less than about 4 square millimeters and having a density of greater than about 2 bonds per square centimeter, said laminate being bulked due to said second layer having from about 15 to about 30 percent more surface area than said first layer per the same unit area of said laminate.

23. A disposable absorbent article, said article comprising:
a liquid-pervious topsheet;
a laminate, said laminate comprising:
a first substantially non-elastic, extensible layer, and
a second layer, said second layer comprising a nonwoven material having a basis weight of from about 5 grams per square meter to about 60 grams per square meter, and being prebonded by a plurality of first spaced-apart bond sites to form first bonded and first unbonded areas, said second layer being attached to said first layer with a plurality of second spaced-apart bond sites to form a bulked laminate with a plurality of second bonded and second unbonded areas, said second bonded and second unbonded areas together defining a surface area of said bulked laminate, said second bonded areas covering from about 8 to about 20 percent of said surface area, at least 50 percent of said second bonded areas having a size of less than about 4 square millimeters, and having a density of greater than about 2 bonds per square centimeter, said laminate being bulked due to said second layer having from about 15 to about 30 percent more surface area than said first layer per the same unit area of said laminate; said laminate defining at least a portion of an outer surface of said article;
an absorbent core located between said topsheet and said laminate, and
a hook component joined to said article for releasably engaging with said laminate.

24. The disposable absorbent article according to claim 23 wherein said first layer comprises a polyolefin film.

25. The disposable absorbent article according to claim 23 wherein said second layer is a nonwoven material formed from spunbond fibers.

26. The disposable absorbent article according to claim 25 wherein said spunbond fibers comprise a polyolefin material and have a thickness of about 2.5 denier per filament.

27. A disposable absorbent article according to claim 25 wherein said spunbond fibers have a peak elongation of less than about 300 percent.

28. The disposable absorbent article according to claim 27 wherein said spunbond fibers have a peak elongation of less than about 200 percent.

29. The disposable absorbent article according to claim 23 wherein said first spaced apart bond sites are formed by the application of thermal energy.

30. The disposable absorbent article according to claim 29 wherein said first spaced apart bond sites cover from about 3 to about 35 percent of a surface area of said second layer.

31. The disposable absorbent article according to claim 30 wherein said first spaced apart bond sites cover from about 5 to about 15 percent of said surface area of said second layer.

32. The disposable absorbent article according to claim 30 wherein said first bonded areas have a size of from about 0.3 square millimeter to about 2.0 square millimeters.

33. The disposable absorbent article according to claim 32 wherein said first bonded areas have a size of from about 0.5 square millimeter to about 1.0 square millimeter.

34. The disposable absorbent article according to claim 30 wherein at least 50 percent of said first bonded areas have a size of from about 0.5 square millimeter to about 0.8 square millimeter.

35. The disposable absorbent article according to claim 34 wherein at least 90 percent of said first bonded areas have a size of from about 0.5 square millimeter to about 0.8 square millimeter.

36. The disposable absorbent article according to claim 32, 33, 34, or 35 wherein said first bonded areas have a bond density of from about 5 to about 20 bonds per square centimeter.

37. The disposable absorbent article according to claim 23 wherein at least about 75 percent of said second bonded areas have a size of less than about 4 square millimeters.

38. The disposable absorbent article according to claim 23 wherein at least about 90 percent of said second bonded areas have a size of less than about 4 square millimeters.

39. The disposable absorbent article according to claim 36 wherein said second bonded areas have a size of less than about 2 square millimeter.

40. The disposable absorbent article according to claim 23 wherein said second bonded areas have a size of less than about 2 square millimeters and a density of from about 7 to about 10 bonds per square centimeter.

41. The disposable absorbent article according to claim 23, 37, 38 or 40 wherein said second bonded areas are generally uniformly spaced from one another.

42. A disposable absorbent article according to claim 23 wherein said first layer is a polyolefin film and said second layer is a nonwoven material formed from spunbond fibers and the temperature at which the onset of melting of said first layer occurs is greater than the temperature at which the onset of melting of said second layer occurs.

43. A disposable absorbent article according to claim 23 wherein said laminate is water impervious.

44. A disposable absorbent article, said article comprising a liquid-pervious topsheet;

a laminate, said laminate comprising:
  a first substantially non-elastic, extensible layer, and
  a second layer, said second layer comprising a nonwoven material having a basis weight of from about 15 grams per square meter to about 30 grams per square meter, and being prebonded by a plurality of first spaced-apart bond sites to form first bonded and first unbonded areas, said second layer being attached to said first layer with a plurality of second spaced-apart bond sites to form a bulked laminate with a plurality of second bonded and second unbonded areas, said second bonded and second unbonded areas together defining a surface area of said bulked laminate, said second bonded areas covering from about 8 to about 20 percent of said surface area, at least 90 percent of said second bonded areas having a size of less than about 4 square millimeters and having a density of greater than about 2 bonds per square centimeter, said laminate being bulked due to said second layer having from about 15 to about 30 percent more surface area than said first layer per the same unit area of said laminate; said laminate defining at least a portion of an outer surface of said article;

an absorbent core located between said topsheet and said laminate, and a hook component joined to said article for releasably engaging with said laminate.

* * * * *